United States Patent [19]

Degner et al.

[11] Patent Number: 4,950,369
[45] Date of Patent: Aug. 21, 1990

[54] PREPARATION OF TETRALIN DERIVATIVES, AND NOVEL TETRALIN DERIVATIVES

[75] Inventors: Dieter Degner, Dannstadt-Schauernheim; Bernd Potzolli, Bad Durkheim; Lothar Janitschke, Kleinniedesheim, all of Fed. Rep. of Germany

[73] Assignee: BASF Aktiengesellschaft, Ludwigshafen, Fed. Rep. of Germany

[21] Appl. No.: 338,109

[22] Filed: Apr. 14, 1989

[30] Foreign Application Priority Data

Apr. 27, 1988 [DE] Fed. Rep. of Germany ....... 3814180

[51] Int. Cl.$^5$ .............................................. C25C 3/00
[52] U.S. Cl. ........................................ 204/78; 204/72; 204/59 R
[58] Field of Search ............................... 204/78, 59 R

[56] References Cited

U.S. PATENT DOCUMENTS

| | | | |
|---|---|---|---|
| 4,318,783 | 3/1982 | Buhmann | 204/79 |
| 4,354,904 | 10/1982 | Malloy et al. | 204/78 |
| 4,539,081 | 9/1985 | Degner et al. | 204/78 |
| 4,760,174 | 7/1988 | Frickel et al. | 562/462 |
| 4,820,389 | 4/1989 | Degnar et al. | 204/78 |

Primary Examiner—John F. Niebling
Assistant Examiner—Steven P. Marquis
Attorney, Agent, or Firm—Keil & Weinkauf

[57] ABSTRACT

A process for the preparation of a tetralin derivative of the formula

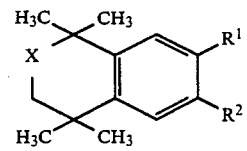

where X is a —CH$_2$—, —CH(OH)— or —CO— group, R$^1$ is one of the groups —COCH$_3$, —CH(OR$^3$)$_2$ or —CHO, R$^2$ is hydrogen or methyl and R$^3$ is alkyl of 1 to 4 carbon atoms, by electrochemical oxidation of a compound of the formula

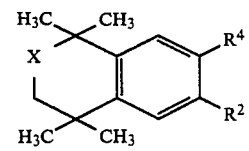

where R$^4$ is methyl or ethyl and X and R$^2$ have the abovementioned meanings, and novel tetralin derivatives.

1 Claim, No Drawings

PREPARATION OF TETRALIN DERIVATIVES, AND NOVEL TETRALIN DERIVATIVES

The present invention relates to a novel process for the preparation of tetralin derivatives by electrochemical oxidation, and novel tetralin derivatives.

We have found that tetralin derivatives of the formula

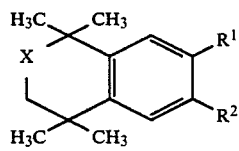

where X is a —CH$_2$—, —CH(OH)— or —CO— group, R$^1$ is one of the groups —COCH$_3$, —CH(OR$^3$)$_2$ or —CHO, R$^2$ is hydrogen or methyl and R$^3$ is alkyl of 1 to 4 carbon atoms, can advantageously be prepared by subjecting a compound of the formula

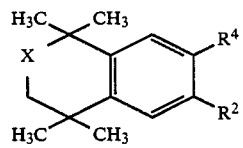

where R$^4$ is methyl or ethyl and X and R$^2$ have the abovementioned meanings, to electrochemical oxidation.

Tetralin derivatives of a similar type are described in, for example, German Laid-Open Application DOS No. 3,434,942. To date, they have preferably been prepared by a double Friedel-Crafts reaction or by a Friedel-Crafts reaction and a Grignard reaction, and they have been obtained in poor yield and with poor selectivity.

The present invention furthermore relates to novel tetralin derivatives of the formulae

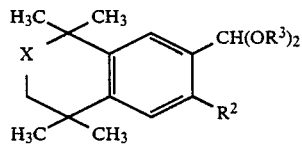

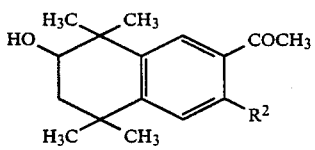

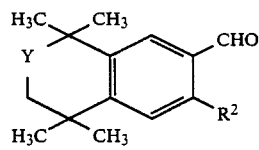

where X is a —CH$_2$—, —CH(OH)— or —CO— group, R$^2$ is hydrogen or methyl, R$^3$ is alkyl of 1 to 4 carbon atoms and Y is a —CH(OH)— or —CO— group.

In these novel tetralin derivatives, the alkyl radical R$^3$ is preferably methyl or ethyl. The novel tetralin derivatives are scents having musk-like properties. They are also intermediates, for example for the preparation of active compounds in the pharmaceutical sector, in particular of retinoids. Thus, retinoids having an improved action spectrum as described in German Laid-Open Application DOS No. 3,434,942 can be synthesized more simply from the novel tetralin derivatives in a conventional manner, for example by a Wittig-Horner or Wittig reaction, in one or more stages.

Examples of novel tetralin derivatives are, for example, the following: 1,2,3,4-tetrahydro-6-dimethoxymethyl-1,1,4,4-tetramethylnaphthalene, 6-diethoxymethyl-1,2,3,4-tetrahydro-1,1,4,4-tetramethylnaphthalene, 1,2,3,4-tetrahydro-6-dimethoxymethyl-1,1,4,4,7-pentamethylnaphthalene, 7-formyl-1,2,3,4-tetrahydro-2-hydroxy-1,1,4,4-tetramethylnaphthalene, 1,2,3,4-tetrahydro-2-hydroxy-7-dimethoxymethyl-1,1,4,4-tetramethylnaphthalene, 7-acetyl-1,2,3,4-tetrahydro-2-hydroxy-1,1,4,4-tetramethylnaphthalene, 1,2,3,4-tetrahydro-7-dimethoxymethyl-1,1,4,4-tetramethyl-2-oxo-naphthalene and 7-formyl-1,2,3,4-tetrahydro-1,1,4,4-tetramethyl-2-oxo-naphthalene.

According to the invention, the tetralin derivatives of the formula I are obtained in a particularly advantageous manner by electrochemical oxidation of the alkyl derivatives of the formula II. In the preparation of tetralin derivatives of the formula I which carry an acetyl group as the radical R, an electrolyte which contains the starting compound of the formula II, where R$^4$ is ethyl, in an aqueous medium is used. In addition to the starting compound, the aqueous electrolyte advantageously also contains a cosolvent and an auxiliary electrolyte. Cosolvents used are those which are stable under the electrolysis conditions, for example nitriles, such as acetonitrile or benzonitrile, ketones, such as acetone or methyl ethyl ketone, or ethers, such as tetrahydrofuran. Preferred cosolvents are alkanols, such as ethanol, isopropanol, tert-butanol or, particularly preferably, methanol. Suitable auxiliary electrolytes are the conventional compounds, such as bases, neutral salts and acids. Examples of bases are alkali metal alcoholates, such as NaOCH$_3$; neutral salts are, for example, fluorides, such as KF, sulfonates, such as KSO$_3$C$_6$H$_5$ or NaSO$_3$C$_6$H$_5$, tetrafluoborates, such as LiBF$_4$, or alkyl sulfates, such as (CH$_3$)$_4$NSO$_4$CH$_3$. Examples of acids which are used are sulfonic acids, such as CH$_3$SO$_3$H or C$_6$H$_5$SO$_3$H, and sulfuric acid. Mixtures of neutral salts and acids are preferred. Benzenesulfonates and benzenesulfonic acids are particularly preferably used. An electrolyte which is particularly suitable for the electrochemical oxidation has, for example, the following composition:

5–25% of a tetralin derivative of the formula II,
5–30% of water,
40–80% of an alkanol,
0.1–5% of an acid and
0.5–5% of a neutral salt.

In the preparation of tetralin derivatives formula I, where R$^1$ is a radical of the formula —CH(OR$^3$)$_2$, the starting material used is an electrolyte which contains the starting compound of the formula II, where R$^4$ is methyl, and an alkanol of the formula R$^3$OH, where R is alkyl of 1 to 4 carbon atoms. The alcoholic electrolyte furthermore advantageously contains an auxiliary electrolyte. Methanol is particularly preferably used as the alkanol. Bases, neutral salts and acids, as mentioned above, can also be used here as auxiliary electrolytes. A particularly suitable electrolyte for the electrochemical oxidation has, for example, the following composition:

3–25% of a tetralin derivative of the formula II,

30–90% of $R^3OH$ and
0.5–5% of an acid or a neutral salt or a mixture of these.

The novel electrochemical oxidation can be carried out in the electrolysis cells conventionally used in industry. Undivided flow-through cells are preferably used. Noble metals, such as Pt, or metal oxides, such as $PbO_2$ or $RuO_2$, are suitable anode materials. Graphite is a preferred anode material. Examples of suitable cathode materials are noble metals, such as platinum, metals such as Ni, Fe or steel, or graphite. The current densities are, for example, 0.5–25, preferably 2–10, $A/dm^2$. The temperatures during the electrolysis can be chosen within wide limits, and electrolysis is preferably carried out at 5° C. or more below the boiling point of the lowest boiling component of the electrolyte. An important advantage of the process is that the compounds of the formula II which are used for the electrochemical oxidation can undergo 80% conversion without the selectivity of the electrochemical oxidation decreasing. After the end of the electrolysis, the electrolytes are separated off by conventional methods, such as distillation, extraction and crystallization, and recycled to the electrolysis. The electrochemical syntheses can be carried out either batchwise or continuously.

The novel tetralin derivatives of the formula III can be used, for example, for the preparation of the aldehydes of the formula

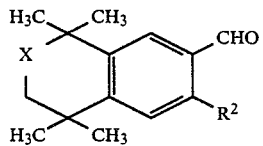

VI where X and $R^2$ have the abovementioned meanings.

The novel aldehydes are obtained by a conventional hydrolysis in which an acetal of the formula III is heated to 30°–100° C., for example in water. The crude acetals as obtained from the electrolysis can also advantageously be hydrolyzed to the novel aldehydes, without intermediate purification.

EXAMPLE 1

Electrochemical synthesis of 7-acetyl-1,2,3,4-tetrahydro-2-hydroxy-1,1,4,4-tetramethylnaphthalene Apparatus: Undivided cell containing 11 electrodes
Anode: Graphite
Electrolyte: 297 g of 7-ethyl-1,2,3,4-tetrahydro-2-hydroxy-1,1,4,4-tetramethylnaphthalene, 6 g of $C_6H_5SO_3H$, 15 g of $NaSO_3C_6H_5$, 300 g of $H_2O$, 2,379 g of $CH_3OH$.
Cathode: Graphite
Electrolysis with 9F/mole of 7-ethyl-1,2,3,4-tetrahydro-2-hydroxy-1,1,4,4-tetramethylnaphthalene
Current density: 2 $A/dm^2$
Electrolysis temperature: 40° C.

During the electrolysis, the electrolyte is pumped at a rate of 400 l/h through the cell via a heat exchanger.

Working up:

After the end of the electrolysis, methanol and water are distilled off under atmospheric pressure and at bottom temperatures of up to 120° C. The residue is extracted with methyl tert-butyl ether, the methyl tertbutyl ether phase is separated off and the methyl tertbutyl ether is distilled off. According to gas chromatographic analysis, the resulting residue (322 g) contains 2.3 g of the starting compound,
22.8 g of 7-(2-methoxyethyl)-1,2,3,4-tetrahydro-2-hydroxy-1,1,4,4-tetramethylnaphthalene and
264 g of 7-acetyl-1,2,3,4-tetrahydro-2-hydroxy-1,1,4,4-tetramethylnaphthalene.

This gives a conversion of 99.2%, a yield of 83.8% and a selectivity of 90.7%. The residue can be recrystallized from 5:1 petroleum ether/ethyl acetate. The 7-acetyl-1,2,3,4-tetrahydro-2-hydroxy-1,1,4,4-tetramethylnaphthalene (mp. 98°–99° C.) was characterized by $^1H$-NMR and $^{13}C$-NMR.

$^1H$-NMR (250 MHz, $CDCl_3$): $\delta = 1.22(s,3H)$, 1.35(s,3H),
1.40(s,3H), 1.48(s,3H), 1.75(sbr.,1H), 1.80(dd, $J_1 = 12Hz, J_2 = 4Hz, 1H$), 1.95(t, $J = 12Hz, 1H$), 2.62(s,3H),
3.92(dd, $J_1 = 12Hz, J_2 = 4Hz, 1H$),
7.43(d, $J = 8Hz$[sic],1H),
7.80(d, $J = 8Hz, 1H$), 8.03(s, 1H).

7-acetyl-1,2,3,4-tetrahydro-1,1,4,4-tetramethyl-2-oxonapthalane was prepared from 7-ethyl-1,2,3,4-tetrahydro-1,1,4,4-tetramethyl-2-oxonaphthalene in a similar manner (mp. 121°–124° C.).

$^1H$-NMR (250 MHz, $CDCl_3$): $\delta = 1.34(s, 6H)$, 1.49(s,6H),
2.62(s,3H), 2.66(s,2H), 7.49(d, $J = 8Hz, 1H$), 7.81 (d, $J = 8HZ, 1H$), 7.98(s, 1H).

EXAMPLE 2

Electrochemical synthesis of 1,2,3,4-tetrahydro-2-hydroxy-7-dimethoxymethyl-1,1,4,4-tetramethylnaphthalene Apparatus: Undivided cell containing 11 electrodes Anode: Graphite Electrolyte: 378 g of 1,2,3,4-tetrahydro-2-hydroxy-1,1,4,4,7-pentamethylnaphthalene, 15 g of $NaSO_3C_6H_5$, 2,607 g of $CH_3OH$, Cathode: Graphite Electrolysis with 6F/mole of 1,1,3,4-tetrahydro-2-hydroxy-1,1,4,4,7-pentamethylnaphthalene Current density: 3.3 $A/dm^2$
Electrolysis temperature: 20°–25° C.

During the electrolysis, the electrolyte is pumped at a rate of 200 l/h through the cell via a heat exchanger.

Working up:

After the end of the electrolysis, methanol is distilled off under atmospheric pressure and at bottom temperatures of up to 120° C., and the residue is filtered at 40° C. to separate off the conductive salt. This gives 518 g of a crude acetal which, after distillation of a sample, is found to consist of 76% by weight of 1,2,3,4-tetrahydro-2-hydroxy-7-dimethoxymethyl-1,1,4,4-tetramethylnaphthalene (bp. 156°–160° C./2 mbar). The product obtained was characterized by $^1H$-NMR.

$^1H$-NMR (250 MHz, $CDCl_3$): $\delta = 1.18(s, 3H)$, 1.30(s,3H),
1.35(s,3H), 1.43(s,3H), 1.75(dd, $J_1 = 12Hz, J_2 = 4Hz, 1H$),
1.87(sbr,1H), 1.92(t, $J = 12Hz, 1H$), 3.37(s, 6H), 3.92 (d, $J = 12Hz, 1H$), 5.38(s, 1H), 7.27(d, $J = 4Hz, 1H$), 7.33 (d, $J = 4Hz, 1H$), 7.45(s, 1H).

The calculated yield was 81.7%.

EXAMPLE 3

Synthesis of 7-formyl-1,2,3,4-tetrahydro-2-hydroxy-1,1,4,4-tetramethylnaphthalene 360 g of water and 0.5 g of concentrated sulfuric acid are initially taken, and 120 g of 1,2,3,4-tetrahydro-2-hydroxy-7-dimethoxymethyl-1,1,4,4-tetramethylnaphthalene are added. The mixture is then heated to the reflux temperature and the methanol is distilled off. The organic phase is taken up with methyl tert-butyl ether. The methyl tert-butyl ether phase is separated off, the methyl tert-butyl ether is distilled off and the residue is crystallized using petroleum ether/toluene. 89 g of 7-formyl-1,2,3,4-tetrahydro-2-hydroxy-1,1,4,4-tetramethylnaphthalene (mp. 76°–78° C.) are obtained. The product obtained was characterized by $^1$H-NMR. $^1$H-NMR (250 MHz, CDCl$_3$): δ=1.23(s,3H), 1.37(s,3H), 1.41(s,3H), 1.50(s,1H), 1.83(dd, $J_1$=12Hz, $J_2$=4Hz,1H), 1.97(t,J=12Hz,1H), 2.83(sbr.,1H), 3.95(dd,$J_1$=12Hz, $J_2$=4Hz,1H), 7.52(d,J=8Hz, 1H), 7.73(d,J=8Hz,1H), 7.97 (s,1H), 10.03(s,1H)

The yield was 88.9%.

EXAMPLE 4

Electrochemical synthesis of 1,2,3,4-tetrahydro-6-dimethoxymethyl-1,1,4,4-tetramethylnaphthalene Apparatus: Undivided cells containing 11 electrodes
Anode: Graphite
Electrolyte: 1,200 g of 1,2,3,4-tetrahydro-1,1,4,4,6-pentamethylnaphthalene, 40 g of C$_6$H$_5$SO$_3$Na, 6,760 g of CH$_3$OH.
Cathode: Graphite
Electrolysis with 5F/mole of 1,2,3,4-tetrahydro-1,1,4,4,6-pentamethylnaphthalene
Current density: 3.3 A/dm$^2$
Electrolysis temperature: 25° C.

During the electrolysis, the electrolyte is pumped at a rate of 400 l/h through the cell via a heat exchanger.

Working up:

After the end of the electrolysis, methanol is distilled off under atmospheric pressure and at bottom temperatures of up to 120° C. The residue is filtered to separate off C$_6$H$_5$SO$_3$Na (which can be recycled to the electrolysis). The filtrate is subjected to fractional distillation under 2 mbar (top pressure) and at 105°–125° C. (top temperatures). The main fraction consisting of 1,2,3,4-tetrahydro-6-dimethoxymethyl-1,1,4,4-tetramethylnaphthalene passes over at 112° C. After distillation, 8.8 g of 1,2,3,4-tetrahydro-1,1,4,4,6-pentamethylnaphthalene, 81.8 g of 1,2,3,4-tetrahydro-6-methoxymethyl-1,1,4,4-tetramethylnaphthalene, which can be recycled to the electrolysis, and 1,137.3 g of 1,2,3,4-tetrahydro-6-dimethoxymethyl-1,1,4,4-tetramethylnaphthalene are obtained.

This gives the following:
Conversion: 99.3% 1,2,3,4-tetrahydro-1,1,4,4,6-pentamethylnaphthalene
Yield: 5.9% 1,2,3,4-tetrahydro-6-methoxymethyl-1,1,4,4-tetramethylnaphthalene
Yield: 73.1% 1,2,3,4-tetrahydro-6-dimethoxymethyl-1,1,4,4-tetramethylnaphthalene
Selectivity: 78.3% 1,2,3,4-tetrahydro-6-dimethoxymethyl-1,1,4,4-tetramethylnaphthalene

EXAMPLE 5

Electrochemical synthesis of 1,2,3,4-tetrahydro-6-dimethoxymethyl-1,1,4,4,7-pentamethylnaphthalene Apparatus: Undivided cell containing 6 electrodes
Anode: Graphite
Electrolyte: 108 g of 1,2,3,4-tetrahydro-1,1,4,4,6,7-hexamethylnaphthalene, 6.5 g of H$_2$SO$_4$, 3,480 g of CH$_3$OH.
Cathode: Graphite
Electrolysis
with
3.5F/mole of 1,2,3,4-tetrahydro-1,1,4,4,6,7-hexamethylnaphthalene
Current density: 3.3 A/dm$^2$
Electrolysis temperature: 25° C.

During the electrolysis, the electrolyte is pumped at a rate of 200 l/h through the cell via a heat exchanger.

Working up:

After the end of the electrolysis, the discharged electrolysis mixture is neutralized with NaOCH$_3$. Thereafter, methanol is distilled off under atmospheric pressure and at bottom temperatures of up to 120° C., the residue is filtered off and the filtrate is subjected to fractional distillation under a top pressure of 1 mbar and at top temperatures of from 105° to 125° C. This gives 16.6 g of 1,2,3,4-tetrahydro-1,1,4,4,6,7-hexamathylnaphthalene, 24.0 g of 1,2,3,4-tetrahydro-6-methoxymethyl-1,1,4,4,7-pentamethylnaphthalene, which can be recycled to the hydrolysis, and 50.3 g of 1,2,3,4-tetrahydro-6-dimethoxymethyl-1,1,4,4,7-pentamethylnaphthalene.

This gives:
Conversion: 84.6% 1,2,3,4-tetrahydro-1,1,4,4,6,7-hexamethylnaphthalene
Yield: 19.5% 1,2,3,4-tetrahydro-6-methoxymethyl-1,1,4,4,7-pentamethylnaphthalene
Yield: 36.5% 1,2,3,4-tetrahydro-6-dimethoxymethyl-1,1,4,4,7-pentamethylnaphthalene
Selectivity: 56.0% 1,2,3,4-tetrahydro-6-dimethoxymethyl-1,1,4,4,7-pentamethylnaphthalene

EXAMPLE 6

1,2,3,4-tetrahydro-7-dimethoxymethyl-1,1,4,4-tetramethyl-2-oxonaphthalene 1,2,3,4-tetrahydro-1,1,4,4,7-pentamethyl-2-oxonaphthalene was subjected to electrochemical oxidation similarly to Example 2 to give 1,2,3,4-tetrahydro-7-dimethoxymethyl-1,1,4,4-tetramethyl-2-oxonaphthalene (bp. 150°–154° C./0.3 mbar). After crystallization from n-heptane, 1,2,3,4-tetrahydro-7-dimethoxymethyl-1,1,4,4-tetramethyl-2-oxonaphthalene was obtained as a white solid in a yield of 26.7% (mp. 91°–92° C., GC 98%). The acetal was characterized by $^1$H- and $^{13}$C-NMR. $^1$H-NMR (250 MHz, CDCl$_3$): δ=1.32(s,6H), 1.47(s,6H), 2.67(s,2H), 3.38(s,6H), 5.42(s,1H), 7.33(d,J=8Hz,1H), 7.40(s,1H), 7.45(s,1H).

EXAMPLE 7

7-Formyl-1,2,3,4-tetrahydro-1,1,4,4-tetramethyl-2-oxonaphthalene

The hydrolysis of 1,2,3,4-tetrahydro-7-dimethoxymethyl-1,1,4,4-tetramethyl-2-oxonaphthalene to 7-formyl-1,2,3,4-tetrahydro-1,1,4,4-tetramethyl-2-oxonaphthalene was carried out similarly to Example 3. The aldehyde was obtained as a white crystalline solid in a yield of 95% (mp. 82°–84° C., GC 98%). It was characterized by $^1$H- and $^{13}$-NMR. $^1$H-NMR (250 MHz, CDCl$_3$): δ=1.37(s,6H), 1.52(s,6H), 2.70(s,2H), 7.63(d,J=8Hz,1H), 7.80(d,J=8Hz,1H), 7.93(s,1H), 10.08(s,1H).

We claim:

1. A process for the preparation of tetralin derivatives of the formula Ib

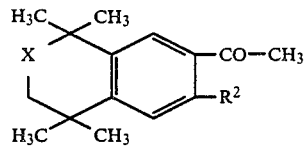

where X is a —CH$_2$—, —CH(OH)— or —CO—group, R$^2$ is hydrogen or methyl, which process comprises subjecting a compound of the formula IIb

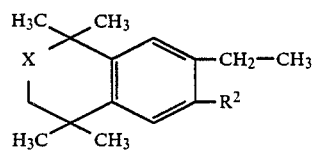

to electrochemical oxidation in an aqueous medium.

* * * * *